United States Patent
Wakamatsu

(10) Patent No.: US 7,332,346 B2
(45) Date of Patent: Feb. 19, 2008

(54) METHOD OF COLLECTING CHEMICALLY CONTAMINATING IMPURITY CONSTITUENTS CONTAINED IN AIR

(75) Inventor: Hidetoshi Wakamatsu, Miyagi (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 741 days.

(21) Appl. No.: 10/284,269

(22) Filed: Oct. 31, 2002

(65) Prior Publication Data

US 2003/0194816 A1    Oct. 16, 2003

(30) Foreign Application Priority Data

Apr. 11, 2002    (JP)    .............. 2002-109119

(51) Int. Cl.
G01N 30/00    (2006.01)
(52) U.S. Cl. .............. 436/175; 436/178; 422/83; 422/88; 422/99; 422/100; 422/101
(58) Field of Classification Search .............. 422/83, 422/88, 89, 99, 100, 101, 102, 103; 436/178, 436/174, 175
See application file for complete search history.

(56) References Cited

U.S. PATENT DOCUMENTS 5,628,900 A * 5/1997 Naito .............. 210/223
5,650,560 A * 7/1997 Troost .............. 73/23.41
5,825,036 A * 10/1998 Ishikawa .............. 250/492.1
5,935,302 A * 8/1999 Ju et al. .............. 96/4

FOREIGN PATENT DOCUMENTS

| JP | 01-203968 | 8/1989 |
| JP | 2000-088718 | 3/2000 |
| JP | 2002-510396 | 4/2002 |

\* cited by examiner

Primary Examiner—Jill Warden
Assistant Examiner—Samuel P Siefke
(74) Attorney, Agent, or Firm—Rabin & Berdo, PC

(57) ABSTRACT

The method is intended to detect with high sensitivity and high accuracy chemically contaminating impurities in which there exist chemically contaminating impurity constituents of basic series, acidic series, and organic substance series, in gaseous and particle states, and constituents of compounds thereof, contained in air inside a clean room, as constituents having every property. To this end, ions composed of various cations and anions, constituting the chemically contaminating impurities in fine particle, gaseous, or molecular state, are caused to continuously undergo dissolution reaction and dissociation reaction in a solution in sequence from those constituting salts having strong solubility or strong dissociative tendency.

3 Claims, 2 Drawing Sheets (a) : COLLECTION / DETECTION APPARATUS (a) : COLLECTION / DETECTION APPARATUS (b) : CHEMICALLY CONTAMINATING IMPURITY
CONSTITUENTS REMOVAL APPARATUS
AND COLLECTION / DETECTION APPARATUS

METHOD OF COLLECTING CHEMICALLY CONTAMINATING IMPURITY CONSTITUENTS CONTAINED IN AIR

BACKGROUND OF THE INVENTION

The present invention relates to a technique for detection of trace amounts (at a ppb to ppt level in concentration) of water-soluble chemically contaminating impurity constituents contained in air inside a clean room. The invention is suitably applied to a method of detecting chemically contaminating impurity constituents in a gaseous or molecular state, evolved from constituent members of a building used as a clean room of a semiconductor manufacturing plant, or manufacturing equipment installed inside the clean room, chemicals used in a manufacturing process, constituent components of auxiliary facilities such as service supply facilities, humans themselves, and so forth, including, for example, chemically contaminating impurity constituents of acidic, basic, condensate (organic substance) series, and dopant series, and constituents of compounds thereof.

As for control of contamination on the surface of semiconductor silicon wafers, it has become important to control surface contamination (cleanliness), surface shape, and residual surface distortion (crystallinity). In a manufacturing process at a semiconductor manufacturing plant and a liquid crystal manufacturing plant, besides adverse effects of fine particle contamination and metallic contamination, chemical contamination such as adsorption contamination, chemical reaction contamination, or condensation contamination of chemically contaminating impurity constituents on the surface of silicon wafers and lenses for the manufacturing equipment such as photolitho stepper, acting as factors of deterioration in reliability and yield, has given adverse effects on the surface of products (silicon wafers) processed in a manufacturing process line, thereby causing problems of various quality deteriorations. Examples of factors causing such quality deteriorations include various chemically contaminating substances in gaseous or molecular state, present in air inside the clean room, and evolved from sources of evolution such as the constituent components of the building, the manufacturing equipment, the chemicals used in the manufacturing process, the constituent components of the auxiliary facilities, humans, etc. and compounds thereof.

More specifically, in the air inside the clean room, there exist not only fine particles but also four species of constituents as chemically contaminating impurity constituents present in mixed state, which can be classified as follows, although this is dependent on variation in process conditions of a manufacturing process line:

1. acidic series substances: corrosive substances having a chemical reaction behavior such as one so as to accept electrons (hydrofluoric acid HF, sulfur oxides SOx, nitrogen oxides NOx, etc.)
2. basic series substances: corrosive substances having a chemical reaction behavior such as one so as to donate electrons (ammonia NH3, amine, etc.)
3. organic series substances: chemical substances having a boiling point higher than room temperature under normal pressure, and undergoing condensation on a clean surface (siloxane, phthalate, HMDS, BHT, etc.)
4. dopant series substances: chemical elements having tendency of causing a change in the electrical characteristic of semiconductor devices such as a transistor and capacitor (boron B, phosphorus P, etc.)

These chemically contaminating impurity constituents in gaseous or molecular state undergo chemical reaction with each other or condensation growth due to a change in environmental conditions inside the clean room, and are transformed into fine particles or compounds in gaseous or molecular state, having different properties, to be thereby adhered to the surface of wafers during a manufacturing process as surface contaminating constituents, thus creating a cause for unstableness in process conditions or a cause for deterioration in yield.

In normal operating conditions, there always occurs evolution of these chemically contaminating impurity constituents in a constant amount and in a constant concentration in a steady state of circulating air of an air conditioning unit of a circulating system flowing along the flowing direction, and the chemically contaminating impurity constituents are carried directly to wafers, a container for transporting the wafers, and the surface of lenses disposed in a manufacturing equipment, which are exposed to an air flow path, to be thereby adhered or adsorbed thereto due to physical or chemical reactions. Further, in operating conditions of manufacturing equipment in an unsteady state as well, there occurs evolution of chemically contaminating impurity constituents in a considerably larger amount than in a normal case, and the chemically contaminating impurity constituents are carried to wafers, a container for transporting the wafers, the surface of glass, and the surface of lenses inside a stepper equipment, which are exposed to the air in the cleaning room, to be adhered or adsorbed thereto due to physical and chemical reactions.

As a method of detecting impurities in the form of fine particles floating in air among the chemically contaminating impurity constituents, there has been known a physically counting method by a laser scattering technique, using a particle counter. Further, as a method of measuring water-soluble chemically contaminating impurity constituents affecting wafer quality due to primary chemical reactions, there has been known a method employing the impinger method for dissolving impurity constituents in pure water, and the ion chromatography for subsequently identifying the impurity constituents. Still further, as a method of detecting chemically contaminating impurity constituents of acidic, basic, condensate (organic substance), and dopant series, respectively, there has been known a detection method combining the solid abstraction method for physically adsorbing these impurity constituents to adsorbents with the gas chromatography.

As for a method of detecting impurity constituents contaminating the surface of wafers, there has been known the liquid abstraction method for dissolving the impurity constituents in a chemical liquid (for example, hydrofluoric acid, and so forth) as a method of measuring water-soluble chemically contaminating impurity constituents affecting wafer quality due to secondary chemical reactions. Further, as a method of detecting organic substances, there have been known a detection method combining the solid abstraction method for physically adsorbing these impurity constituents to adsorbents with the TOC analytical method, and the SIMS method. Still further, as a method of detecting impurity constituents of inorganic metal ions, there have been known the vapor-phase cracking method and the total reflection fluorescent X ray analysis method. Yet further, as a analytical method of detecting adsorbing molecules, there have been known the thermal desorption spectroscopy (TDS) and the Time of Flight Mass Spectroscopy (TOF-SIMS) analytical method. Any of the detection methods described above has the following feature.

Firstly, in the case of detecting fine particles, fine particles down to 0.05 μm in grain size can be counted by the laser scattering method, however, an interrelation between a shape of the fine particles and a counting device is important. As a method of finding out the concentration of ultrafine particles, in number, there is available a condensation nucleus counter. This is a method wherein an atmosphere around ultrafine particles is turned into supersaturation state by any method using alcohol, water vapor, and so forth, causing vapor around the ultrafine particles to undergo condensation growth to thereby optically detect the number of the ultrafine particles.

In the case of detecting organic substances, a method of absorbing organic carbons is important in the absorbing method. With the SIMS analytical method, analysis of bacteria, and so forth, and determination of contaminated spots are important.

In the case of detecting inorganic metal ion impurities, evaluation of concentration, down to a level of $10^9$ atoms/cm$^2$, and nondestructive evaluation of distribution within a wafer surface are feasible, however, dependency on recovered liquid species, and high sensitivity are important.

Further, in the case of detecting adsorbing molecules, evaluation of an adsorption state, and quantification of water molecules, contaminating constituents, and so forth, are important in the TDS analytical method. With the TOF-SIMS analytical method, analysis of light elements is feasible, however, high sensitivity and quantification are important.

However, there is the following problem with any of the detection methods described above, such as the laser scattering method, chemical reaction adsorption-separation method, electron beam or X-ray irradiation method, and thermal programmed desorption analytical method.

Firstly, in the case of detecting fine particles by the laser scattering method, fine particles less than 0.05 μm in grain size can not be counted, and it is necessary to check the interrelation between the shape of the fine particles and the counting device. There occurs a problem in that sufficient scattering signals can not be obtained in terms of an S/N ratio when a grain size is not more than 0.1 μm.

Further, in the case of extracting the organic substances by the adsorption-separation method, the method of extracting the organic carbons is difficult to perform, and there is a problem with the Secondary Ion Mass Spectroscopy (SIMS) analytical method in that analysis of bacteria, and so forth, and determination of the contaminated spots are not possible to implement.

In the case of detecting metal ion impurities by use of electron beam or X-ray, evaluation of concentration at a level less than $10^9$ atoms/cm$^2$ is unfeasible, and there is a problem with dependency on the recovered liquid species, and high sensitivity. This method has a problem in that it is dependent on the shape and species of fine particles, and microscopic asperities on a wafer surface are detected as measured values.

Further, in the case of detecting the adsorbing molecules by the TDS analytical method, quantification and identification is difficult to achieve due to a change in adsorption and release states of water molecules, and so forth, and a change in surface property and crystalline condition of adsorption surfaces. For example, it is not possible to perform analysis of heavy elements by the TOF-SIMS analytical method, which has a problem with high sensitivity and quantification.

That is, with any of the detection methods described in the foregoing, there is a problem in that detection is effected by reaction, decomposition, or dissociation, taking place only once, and consequently, it is not possible to separate interfering constituents simultaneously interfering with each other.

SUMMARY OF THE INVENTION

The invention is intended to detect with high sensitivity and high accuracy chemically contaminating impurities in which there exist chemically contaminating impurity constituents of basic series, acidic series, and organic substance series, in gaseous and particle states, and constituents of compounds thereof, contained in air inside a clean room, as constituents having every property.

To this end, ions composed of various cations and various anions, constituting contaminating impurities in fine particle, gaseous, or molecular state, are caused to continuously undergo dissolution reaction and dissociation reaction in a solution in sequence from those constituting salts having strong solubility or strong dissociative tendency.

DETAILED DESCRIPTION OF PREFERRED EMBODIMENTS

First Embodiment

Figure 1A:
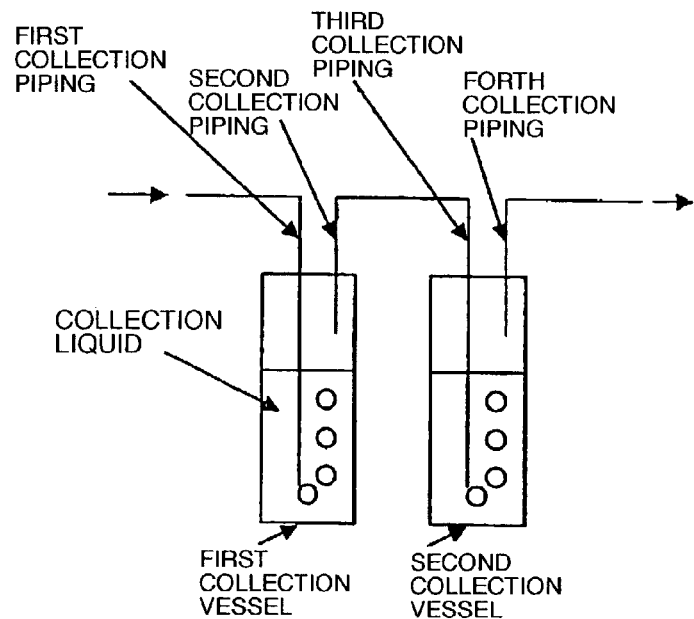
FIGS. 1(a) and 1(b) are schematic views illustrating broadly a first embodiment of the invention.
Figure 1B:
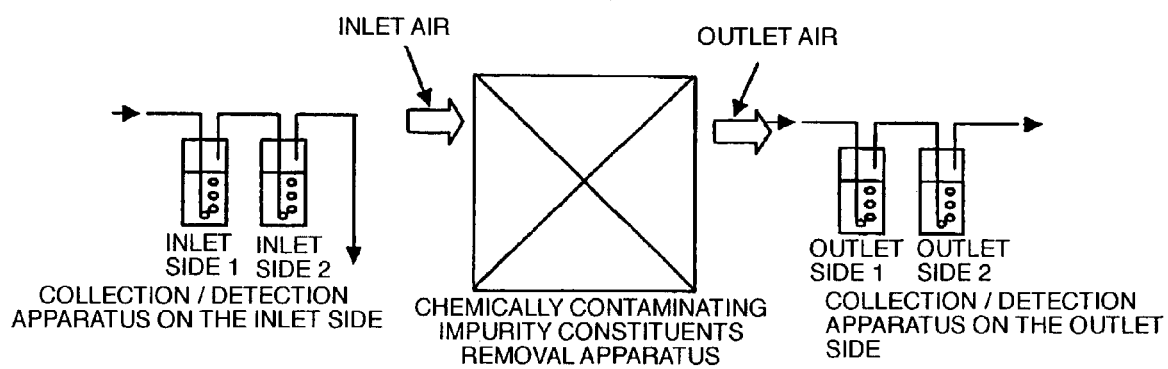
Figure 2:
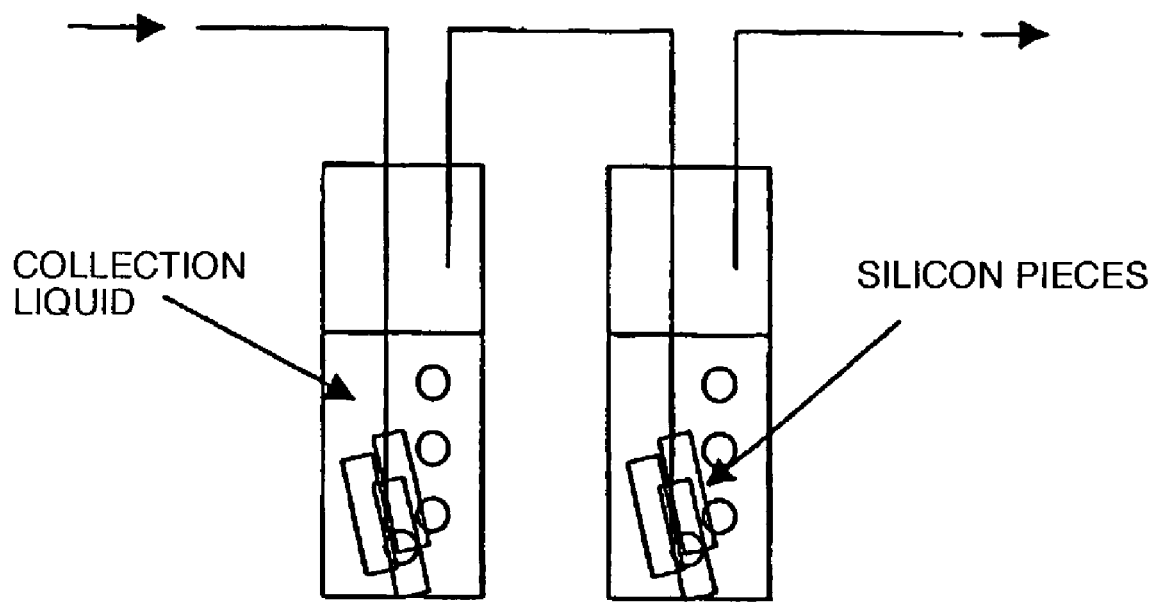
FIG. 2 is a schematic view illustrating broadly a second embodiment of the invention.

FIG. 1(a) is a schematic illustration showing a collection/detection apparatus for carrying out a first embodiment of a detection method according to the invention, for collecting chemically contaminating impurity constituents contained in circulating air inside a clean room for semiconductor manufacturing plants, incorporating the function of collecting the chemically contaminating impurity constituents contained in air. FIG. 1(b) is a schematic illustration showing an overall system wherein the collection /detection apparatus is installed on the inlet side and the outlet side of a chemically contaminating impurity constituent's removal apparatus, respectively.

As shown in FIG. 1(a), the method for collection and detection is carried out with a system configuration wherein (1) a first collection piping, (2) a first collection vessel containing a first collection liquid, (3) a second collection piping, (4) a third collection piping, (5) a second collection vessel containing a second collection liquid, and (6) a fourth collection piping are disposed in that order sequentially from the upstream side.

With a collection and processing unit of the first and second collection vessels, respectively, according to the present embodiment, the collection vessel in respective stages is filled up with new activated water. For the collection piping in respective processing stages, use is made of piping having such a tip structure that micro-air-like bubbles can be generated so as to maximize vapor-liquid contact efficiency.

At the collection and processing unit in a first stage, basic caption constituents in air, particularly $NH_4$ ions having high solubility, and acidic and condensating (organic substance series) anion constituents in air, particularly, negatively charged ions of $NO_2$ and negatively charged ions (bivalent) of $SO_4$, having high chemical activation tendency, that is, having high dissociation tendency, can be efficiently dissolved in a liquid, and dissociated to be thereby collected.

At the collection and processing unit in a second stage, a portion of the acidic anion constituents, not dissociated by the agency of interfering ions in a solution in the first stage, particularly negatively charged F ions having the highest activation tendency, and a portion of the acidic and condensating (organic substance series) anion constituents, not dissociated by the agency of the interfering ions in the solution in the first stage, particularly negatively charged $NO_3$ ions having low solubility, can be dissociated in the liquid to be thereby collected.

FIG. 1(b) shows an example of a configuration wherein the collection/detection apparatus using the new activated water for the collection liquid is installed on the inlet side and outlet side of the chemically contaminating impurity constituents removal apparatus, respectively, to thereby examine performance thereof for removing the chemically contaminating impurity constituents contained in the air inside the clean room in order to check operation effects of the new activated water. Table 1 shows analysis results of the chemically contaminating impurity constituents as detected from the new activated water used as the collection liquid. For the sake of comparison, analysis results of the chemically contaminating impurity constituents as detected from pure water used as the collection liquid are also shown therein.

advantageous effects of the second embodiment of the invention can be enhanced more than those for the first embodiment. Still further, as for the number of the collection vessels linked together in series, any number thereof may be used with either the first embodiment or the second embodiment.

Now, the advantageous effects of the invention are recapped as follows. As described hereinbefore, with the invention, there is provided the collection and detection apparatus wherein (1) the first collection piping, (2) the first collection vessel containing the first collection liquid, (3) the second collection piping, (4) the third collection piping, (5) the second collection vessel containing the second collection liquid, and (6) the fourth collection piping are disposed in that order sequentially from the upstream side.

With the use of means for collecting the chemically contaminating impurity constituents, comprising a collection/detection system in the two stages, using the new activated water as the collection liquid, and performing collection and processing at the respective stages, it becomes possible to obtain vapor-liquid contact efficiency, dissolution efficiency, and dissociation efficiency, equivalent to or better than those for the conventional detection method, for the chemically contaminating impurity constituents that have been unable to be quantified and identified by the conventional detection method, by employing a method using a very small and less amount of a liquid for collecting

TABLE 1

Detection Results when pure water and the new activated water are used for the collection liquid, respectively.

|  | Na | $NH_4$ | K | F | $NO_2$ | $NO_3$ | $SO_4$ | Unit |
|---|---|---|---|---|---|---|---|---|
| new activated water |  |  |  |  |  |  |  |  |
| inlet side 1 | 1010.0 | 1880.0 | 503.0 | 680.0 | 5590.0 | 4980.0 | 622.0 | ng/m3 |
| inlet side 2 | 1050.0 | 130.0 | 514.0 | 2400.0 | 330.0 | 1770.0 | 610.0 | ng/m3 |
| outlet side 1 | 1310.0 | 120.0 | 567.0 | 970.0 | 120.0 | 2720.0 | 560.0 | ng/m3 |
| outlet side 2 | 1210.0 | 130.0 | 615.0 | 1000.0 | 320.0 | 2400.0 | 810.0 | ng/m3 |
| pure water |  |  |  |  |  |  |  |  |
| inlet side 1 | 25.0 | 2730.0 | 26.0 | 680.0 | 6350.0 | 594.0 | 86.0 | ng/m3 |
| Inlet side 2 | 285.0 | 130.0 | 170.0 | 1700.0 | 1490.0 | 550.0 | 130.0 | ng/m3 |
| outlet inside 1 | 21.0 | 270.0 | 21.0 | 850.0 | 2060.0 | 270.0 | 110.0 | ng/m3 |
| outlet side 2 | 29.0 | 130.0 | 26.0 | 1000.0 | 130.0 | 130.0 | 130.0 | ng/m3 |

Second Embodiment

A basic system configuration of a collection and detection unit, adopted for a second embodiment of a method of collecting chemically contaminating impurity constituents in air according to the invention, is the same as that in the case of the first embodiment shown in FIG. 1. The second embodiment differs from the first embodiment in that with the second embodiment, for example, silicon pieces used as adsorbents are dipped in a solution inside a collection vessel at respective stages. As a result, detection efficiency for water-soluble organic substances can be enhanced. Further, gas, and using no chemical. Further, by use of the new activated water having chemical function both alkaline and acidic, it is possible to separate every chemically contaminating impurity constituent of acidic, basic, condensating (organic substance), or dopant series, in gaseous and molecular states, that are present in mixed state in the air inside the clean room, in the new activated water for detection, at high dissolution efficiency, high dissociation efficiency, and stable collection efficiency as well as simultaneously, efficiently, and selectively.

Also, by use of the new activated water for the collection liquid, specific ionic constituents only can be separated and detected in the same collection liquid, keeping a state where chemically interfering reactions of respective anions and cations of the contaminating impurity constituents with each other do not occur.

The present invention is not limited to the above embodiments. For example, the invention may intended to provide a method capable of stably separating and detecting with high accuracy water-soluble chemically contaminating impurity constituents that exist in air inside a clean room by a method of collecting the constituents through processing in a plurality of stages, wherein balance in ion makeup is changed, and ions are converted sequentially in descending order of chemical activity thereof into constituents that can be dissolved and dissociated in a solution.

At the same time, the invention is further intended to solve above-described problems with a variety of conventional methods of detection by eliminating drawbacks thereof with respect to quantification and identification of chemical constituents from generation sources of the chemically contaminating impurities while maintaining accuracy equivalent to or higher than that for the conventional detection method.

Activated water for use as a collection liquid is a solution having both alkaline and acidic chemical functions, and is produced by an apparatus comprising a purification part for purifying water quality by causing impurities in a supplied liquid, such as organic substances and so forth, to flock together with the use of activated charcoal, sand, and so forth, and an activation part for activating water quality with the use of high power magnet, magnetite, and a special ceramic irradiating weak electromagnetic waves. The activated water produced with the apparatus made up of the purification part and the activation part is referred to hereinafter as "new activated water" for the sake of convenience. The new activated water is activated water, containing hydrogen ions ($H^+$) and hydroxyl ions ($H_3O_2^-$), and having both acidic and alkaline properties. Further, this is activated water in which a cluster of water molecules is stably rendered smaller to about 10 in terms of the number of water molecules from 50 for the normal case.

In order to achieve the objects of the invention as described above, in a first aspect of the invention, there is provided a method of collecting chemically contaminating impurity constituents contained in air by use a collection system having a configuration for extraction, comprising a first collection vessel capable of passing a target air containing chemically contaminating impurity constituents in gaseous and molecular state therethrough from the upstream towards the downstream, first means for collecting chemically contaminating impurity constituents, capable of dissolving the chemically contaminating impurity constituents in activated water solution by a method of vapor-liquid contact between the activated water solution in the first collection vessel and chemically contaminating impurity constituents in the gaseous and molecular state, contained in a circulating air passing through a first collection piping, a second collection vessel capable of passing a target air containing the chemically contaminating impurity constituents in gaseous state and molecular state therethrough from the upstream towards the downstream; and second means for collecting chemically contaminating impurity constituents, capable of dissolving the chemically contaminating impurity constituents in activated water solution by a method of vapor-liquid contact between the activated water solution in the second collection vessel and chemically contaminating impurity constituents in the gaseous and molecular state, contained in a circulating air passing through a second collection piping, that are linked with each other in succession.

The method of collecting chemically contaminating impurity constituents contained in air according to the invention may use a collection system having a system configuration wherein a collection vessel made of material not causing the chemically contaminating impurity constituents to be eluted in solution is used for the first and second collection vessels, respectively, and the new activated water as a collection liquid is used in the respective collection vessels. If a vapor-liquid contact method for causing a solution to be bubbled directly with a collected air is employed at this point in time as the first means for collecting the chemically contaminating impurity constituents, preferable dissolution and collection efficiency can be obtained. Further, in the case where species of the chemically contaminating impurity constituents contained in air are large in number, it becomes possible to separate and detect the chemically contaminating impurity constituents with high accuracy by employing the new activated water for the collection liquid in the respective collection vessels.

Further, with the second means for collecting the chemically contaminating impurity constituents, adsorbents selectively adsorbing certain constituents such as silicon pieces or PTFE resin pieces are preferably mixed into the activated water solution, whereupon not only a basic gas and acidic gas but also even organic substance constituents can be absorbed and collected, thereby enabling further preferable constituent separation efficiency and detection sensitivity to be obtained.

Furthermore, the method of collecting chemically contaminating impurity constituents contained in air according to the invention may use a collection system having a system configuration wherein a piping made of material not causing the chemically contaminating impurity constituents to be eluted in solution is used for the respective collection pipings, and the collection piping at respective stages is structured so as to cause the new activated water as the collection liquid to be bubbled.

What is claimed is:

1. A method of collecting chemically contaminating impurity constituents contained in air by use of a collection system having a configuration for extraction, comprising:

passing a target air containing chemically contaminating impurity constituents in gaseous state and molecular state therethrough from the upstream towards the downstream in a first collection vessel;

collecting chemically contaminating impurity constituents, capable of dissolving the chemically contaminating impurity constituents in an activated water solution by a method of vapor-liquid contact between the activated water solution in the first collection vessel and chemically contaminating impurity constituents in the gaseous state and molecular state, contained in a circulating air passing through a first collection piping;

passing the target air passed through the first collection vessel from the upstream towards the downstream into a second collection vessel; and collecting chemically contaminating impurity constituents, capable of dissolving the chemically contaminating impurity constituents in the activated water solution by a method of vapor-liquid contact between the activated water solution in the second collection vessel and chemically contaminating impurity constituents in the gaseous state and molecular state, contained in a circulating air passing through a second collection piping, that are linked with each other in succession, wherein the activated water solution is produced with a filter, using as a filler a special ceramic irradiating weak electromagnetic waves, and is used for a collection liquid inside the collection vessel at respective stages;

providing an apparatus including a purification part for purifying water quality by causing impurities in a supplied liquid including organic substances to flock together with a use of at least one of an activated charcoal and sand, and an activation part for activating water quality with use of a high power magnet, magnetite, and the special ceramic irradiating weak electromagnetic waves; and producing the activated water solution by the apparatus;

wherein the first collection vessel collects basic cation constituents and acidic and condensating anion constituents.

2. A method of collecting chemically contaminating impurity constituents according to claim 1, wherein the basic cation constituents includes NH4 ions having high solubility.

3. A method of collecting chemically contaminating impurity constituents according to claim 1, wherein the acidic and condensating anion constituents includes negatively charged ions of NO2 and negatively charged ions (bivalent) of SO4.

* * * * *